United States Patent
Steiner et al.

(10) Patent No.: US 9,017,377 B2
(45) Date of Patent: Apr. 28, 2015

(54) OCCLUDER

(75) Inventors: Claudio Steiner, Schwyz (CH); Jörg Hummen, Kilchberg (CH); Andreas Weishaupt, Ebertswil (CH)

(73) Assignee: Carag AG, Baar (CH)

( * ) Notice: Subject to any disclaimer, the term of this patent is extended or adjusted under 35 U.S.C. 154(b) by 250 days.

(21) Appl. No.: 13/376,723

(22) PCT Filed: Jun. 3, 2010

(86) PCT No.: PCT/CH2010/000147
§ 371 (c)(1),
(2), (4) Date: Dec. 7, 2011

(87) PCT Pub. No.: WO2010/142051
PCT Pub. Date: Dec. 16, 2010

(65) Prior Publication Data
US 2012/0078295 A1  Mar. 29, 2012

(30) Foreign Application Priority Data
Jun. 10, 2009  (CH) ..................................... 0899/09

(51) Int. Cl.
*A61B 17/08* (2006.01)
*A61B 17/00* (2006.01)

(52) U.S. Cl.
CPC ... *A61B 17/0057* (2013.01); *A61B 2017/00575* (2013.01); *A61B 2017/00588* (2013.01);
(Continued)

(58) Field of Classification Search
CPC ..................... A61B 17/0057; A61B 17/12122; A61B 2017/00575; A61B 2017/00588; A61B 2017/00606
USPC ......... 606/151, 153, 155, 157, 158, 200, 213, 606/215, 216
See application file for complete search history.

(56) References Cited

U.S. PATENT DOCUMENTS 5,702,421 A   12/1997  Schneidt
5,709,707 A *  1/1998  Lock et al. ................... 606/213
(Continued)

FOREIGN PATENT DOCUMENTS

CN   2543502   4/2003
CN   1486161   3/2004
(Continued)

OTHER PUBLICATIONS

International Search Report and Written Opinion for International Patent App. No. PCT/CH2010/000147, completed Jun. 28, 2010.

*Primary Examiner* — Kathleen Holwerda
*Assistant Examiner* — Sarah W Aleman
(74) *Attorney, Agent, or Firm* — McDonnell Boehnen Hulbert & Berghoff LLP

(57) ABSTRACT

The invention relates to an occluder for closing a passage in a circulatory system comprising an expandable fixation unit for fixing the occluder on the passage, wherein the occluder can be transferred in the passage from a compact appearance into an expanded appearance. The occluder has a distal and a proximal axial part, in which the fixation unit is pivotally held. According to the invention, the fixation unit comprises distal fixation arms and proximal fixation arms, wherein the distal fixation arms are pivotally held in the distal axial part and the proximal fixation arms are pivotally held in the proximal axial part. The distal and the proximal fixation arms have free ends, which are interconnected by means of connecting members that can be moved relative to the fixation arms, wherein in each case a distal fixation arm is connected to a proximal fixation arm located diagonally opposed thereto. Said occluder is suited in particular for closing a ventricular septal defect (VSD).

15 Claims, 14 Drawing Sheets

(52) U.S. Cl.
CPC .......... *A61B2017/00592* (2013.01); *A61B 2017/00597* (2013.01); *A61B 2017/00601* (2013.01); *A61B 2017/00606* (2013.01); *A61B 2017/00619* (2013.01)

(56) References Cited

U.S. PATENT DOCUMENTS

| | | | |
|---|---|---|---|
| 6,117,159 A | 9/2000 | Huebsch et al. | |
| 6,712,836 B1 | 3/2004 | Berg et al. | |
| 2005/0043759 A1* | 2/2005 | Chanduszko | 606/213 |
| 2005/0065548 A1* | 3/2005 | Marino et al. | 606/213 |
| 2005/0251154 A1 | 11/2005 | Chanduszko et al. | |
| 2005/0267524 A1 | 12/2005 | Chanduszko | |
| 2006/0116710 A1* | 6/2006 | Corcoran et al. | 606/200 |
| 2006/0241687 A1 | 10/2006 | Glaser et al. | |
| 2007/0129755 A1 | 6/2007 | Abbott et al. | |
| 2007/0282430 A1* | 12/2007 | Thommen et al. | 623/1.22 |
| 2008/0262518 A1 | 10/2008 | Freudenthal | |

FOREIGN PATENT DOCUMENTS

| | | |
|---|---|---|
| DE | 29500381 | 7/1995 |
| EP | 0474887 | 3/1992 |
| EP | 1149561 | 10/2001 |
| EP | 1836969 | 9/2007 |
| EP | 1994887 | 11/2008 |
| JP | 2007-504915 | 3/2007 |
| WO | 97/16119 | 5/1997 |
| WO | 01/21246 | 3/2001 |
| WO | 02/38051 | 5/2002 |
| WO | 2005/027752 | 3/2005 |
| WO | 2005/034723 | 4/2005 |
| WO | 2005/074813 | 8/2005 |
| WO | 2005/112779 | 12/2005 |
| WO | 2008/040555 | 4/2008 |
| WO | 2008/153872 | 12/2008 |
| WO | 2009/045702 | 4/2009 |

* cited by examiner

OCCLUDER

CROSS REFERENCE TO RELATED APPLICATIONS

The present application is a U.S. National Phase Application pursuant to 35 U.S.C. §371 of International Application No. PCT/CH2010/000147 filed Jun. 3, 2010, which claims priority to Swiss Patent Application No. 899/09 filed on Jun. 10, 2009. The entire disclosure contents of these applications are herewith incorporated by reference into the present application.

TECHNICAL FIELD

The present invention relates to an occluder.

PRIOR ART

Occluders are implants that are used to close passages in circulatory systems, for example blood vessels or shunt connections, and that are usually positioned and expanded via a sheath introduced into a vein. Occluders are used, for example, to close a persistent ductus arteriosus (PDA), an atrial septal defect (ASD) or a ventricular septal defect (VSD). Other uses in the human or animal body are possible. The form of the occluders is adapted in each case to the corresponding use.

Occluders are known in a wide variety of designs in the prior art. For example, they can be designed as a spiral spring or can open out like an umbrella. They can also close the passage from just one side or from both sides. These occluders can usually be brought into an elongate shape, such that they can be advanced by means of the catheter to the passage that is to be closed. The occluder is released there, and it recovers its expanded shape of use either automatically or in a guided manner.

An occluder that can be opened in a guided manner, and that can thus be positioned optimally in the passage, is disclosed in WO 2005/074813.

US 2005/0251154 discloses an occluder with two spiral springs, which come to lie one on each side of the passage and fix the occluder in this position. The spiral springs are connected to each other at one end via a yoke.

U.S. Pat. No. 6,117,159 describes an occluder in the form of a hollow cylinder. The hollow cylinder is slit in the longitudinal direction, and the continuous slits terminate at a distance from the two ends of the cylinder and also leave the central area free. Plane struts are thus formed. Circumferential notches are present at the ends of the struts and in the central area thereof and act as film hinges. If the two ends of the hollow cylinder are now moved toward each other, the struts fold out and convert the occluder to an expanded form of appearance with two mutually opposite fixation planes. Similar arrangements are disclosed in WO 2009/045705 and WO 2005/112779.

EP 1 836 969 also discloses an occluder, in which the fixation struts are provided with hinges.

In EP 0 474 887, the occluder has two mutually opposite textile circular surfaces with a frame. The two circular surfaces are connected to each other by threads.

WO 2005/034723 likewise discloses an occluder with two membranes, which are arranged at a distance from each other on a central cylinder. Wires extend from the frame of the first membrane to the frame of the second membrane, said wires passing through the central cylinder.

Defects in the ventricular septum differ greatly from defects in the atrium. In the ventricular septum, an occluder is exposed to a higher pressure. Moreover, the thickness of the septum varies more than in the atrium. In particular, the thickness is in some parts considerably greater than in the atrium. In adults, it can usually measure up to 15 mm. Moreover, the available space is different and also very much more confined than in the atrium. The occluders known in the prior art are often not optimally adapted to these circumstances.

DISCLOSURE OF THE INVENTION

It is an object of the invention to make available an occluder that is suitable in particular for closing a ventricular septal defect (VSD).

The occluder according to the invention for closing a passage in a circulatory system has an expandable fixation unit for fixing the occluder on the passage, wherein the occluder can be transferred in the passage from a compact form of appearance to an expanded form of appearance. The occluder has a distal axial part and a proximal axial part, in which parts the fixation unit is held pivotably. According to the invention, the fixation unit has distal fixation arms and proximal fixation arms, wherein the distal fixation arms are held pivotably in the distal axial part and the proximal fixation arms are held pivotably in the proximal axial part. The distal and the proximal fixation arms have free ends, which are connected to one another via connecting members that are movable relative to the fixation arms, wherein in each case a distal fixation arm is connected to a proximal fixation arm. Fixation arms lying diametrically opposite each other are preferably interconnected in each case.

Here, proximal means in the direction of the physician, and distal means in the direction away from the physician, that is to say toward the patient.

This occluder has the advantage that it has relatively small dimensions both in the compact, elongate state and also in the expanded state and yet can withstand the high pressure in the area of the ventricular septum. A further advantage is that the occluder in the expanded position of use bears relatively flat on both sides of the ventricular septum, does not protrude or only slightly protrudes into the ventricle, and does not disturb the function of the heart valve. It is also advantageous that the occluder can be opened and expanded in a guided manner and can thus be positioned optimally in the passage.

In the compact state, the occluder according to the invention is relatively short compared to the known occluders. Typical lengths are 20 mm to 50 mm, preferably 30 mm. In this way, upon introduction into the ventricular septum, the occluder can be better guided round tight curves.

In the expanded state, its diameter measures approximately 10 mm to 30 mm, preferably 20 mm. This diameter is therefore also smaller than the usual diameters of the known occluders used for the same purpose.

In a preferred embodiment, the connecting members extend independently of one another between the individual distal and proximal fixation arms. They preferably intersect in one area. This area preferably lies approximately centrally between the proximal axial part and the distal axial part in the longitudinal direction of the occluder. In a first embodiment, this intersection area is free of other elements. In another embodiment, the connecting members extend in an individually displaceable manner in a first sleeve that surrounds them jointly in this area.

In a preferred embodiment, each of the fixation arms is bow-shaped or U-shaped with two branches and a bridge joining these branches. The two branches have free ends, which are held pivotably in the proximal or distal axial part. The bridge forms the free end of the fixation arm. This U-shaped design gives stability to the fixation arms, and they can be easily assembled and easily connected to the connecting members.

The bridge is preferably enclosed by a second sleeve, in which case the bridge is held pivotably in the second sleeve. A connecting member is secured on each second sleeve, preferably connected integrally or welded thereto. A joint or a hinge is thus easily obtained that permits the relative movement between fixation arm and connecting member. Preferably, the bridge is approximately rectilinear, such that the second sleeve is held in its position on the fixation arm without further auxiliary means. If the bridge is round, the second sleeve can be fixed in its position by two clamping sleeves for example. These two clamping sleeves are in each case arranged on an end face of the hinge sleeve.

In a preferred embodiment, the fixation arms consist of wires, preferably made of nitinol or of a resorbable material. The connecting members can likewise consist of wires or of strings.

If the connecting members consist of wires, they then support the movement of the fixation arms during the expansion and force the fixation arms into the opened position thereof.

If the connecting wires consist of strings, for example of polypropylene (PP) or polylactate, they then limit the maximum distance between the distal and the proximal fixation arms and also limit the angle of expansion of the fixation arms. In this embodiment, the fixation arms open without further help. They are for this purpose mounted at an angle in the distal axial part and in the proximal axial part. This angle is reduced in the compact state achieved by the effect of an external force. In the absence of this external force, the angle is adopted again by the spring action or elasticity of the wires.

The proximal axial part and the distal axial part are preferably designed as interconnectable coupling parts that can be inserted one inside the other and fixed. In this way, they fix the occluder in its expanded form of appearance, and the distance between the distal and the proximal fixation arms can be chosen by the physician.

The distal and the proximal fixation arms are preferably of the same size, and the occluder has mirror symmetry with respect to the fixation unit. However, the occluder can also be made asymmetrical, or the fixation arms of the distal and/or proximal side can have different sizes and/or shapes from each other.

Moreover, instead of the wires of the fixation arms, flat bows or arms can also be used. The wires can also have shapes other than the U-shape.

The occluder preferably has at least one closure body for closing the passage. This closure body is preferably a membrane, a tampon or a balloon. If the closure body is a membrane, it can then preferably be brought to the expanded form of appearance by means of the fixation arms. The tampon is preferably compressible and elastic, such that it can automatically adopt its expanded shape. If the closure body is a balloon, the latter preferably extends from the proximal axial part to the distal axial part and is secured on these two parts. The balloon surrounds the fixation arms and the connecting members and is preferably brought to its expanded state by the fixation arms.

The closure body, in particular the tampon, is preferably arranged in an area that is defined on one side by the distal fixation arms and on an opposite side by the proximal fixation arms. In this way, the closure body is located in the passage itself and not on an outer face of the passage. This arrangement of the closure body can also be used in occluders other than those described here and is claimed here as an independent invention. An occluder with at least one closure body arranged in this way permits rapid and optimal closure, even under high pressures. It is advantageous that it does not protrude or only slightly protrudes into the ventricle.

The connecting members define the maximum distance between the proximal and the distal fixation arms and support the expansion of the occluder. However, in one embodiment, no connecting members are present. This embodiment is likewise claimed as an independent invention, which can have all of the abovementioned variants and combinations without connecting members.

These occluders according to the invention are suitable in particular for closing a ventricular septal defect (VSD). However, they can also be used in other areas, particularly the abovementioned areas. They permit an anatomically and physiologically optimized closure of a defect.

Further embodiments are set forth in the dependent claims.

BRIEF DESCRIPTION OF THE DRAWINGS

Preferred embodiments of the invention are described below with reference to the drawings, which serve only for explanatory purposes and are not to be interpreted as limiting the invention. In the drawings.

DESCRIPTION OF PREFERRED EMBODIMENTS

Figure 1:
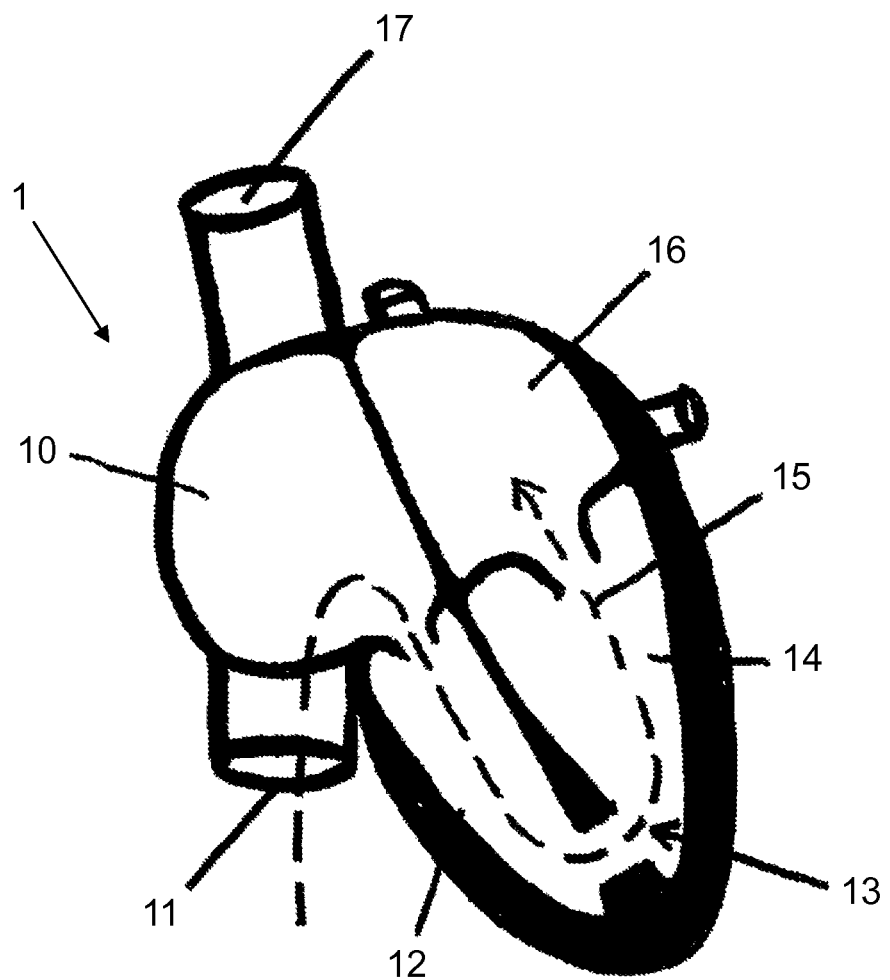
FIG. 1 shows a schematic view of a human heart with a ventricular septal defect (VSD)

FIG. 1 shows a view of a human heart 1 with a ventricular septal defect (VSD). The right atrium is designated by reference number 10, the inferior vena cava by 11, the right ventricle by 12, the ventricular septal defect by 13, the left ventricle by 14, the left atrium by 16, and the superior vena cava by 17. The broken arrow 15 indicates the path by which a guide wire is inserted. In this way, an occluder can be brought to the site of the defect by means of a catheter system and can close the defect.

Figure 2:
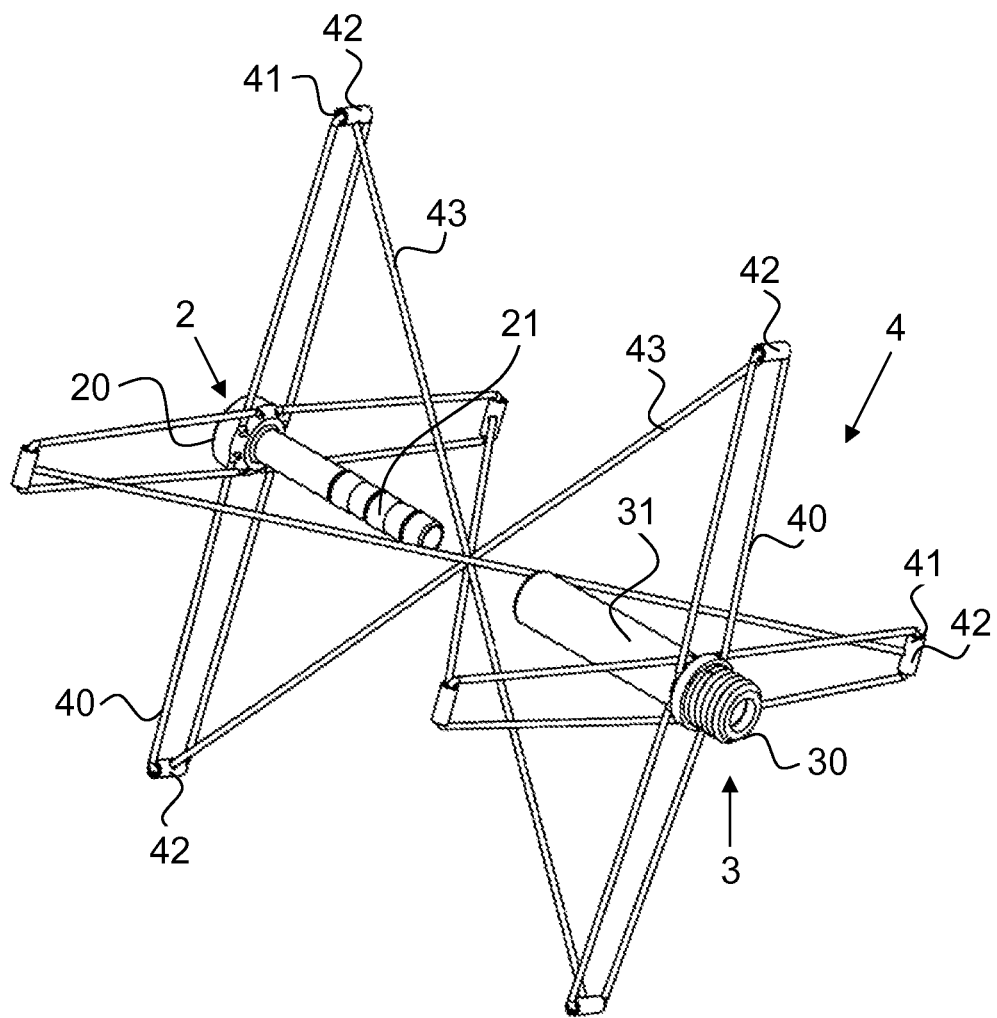
FIG. 2 shows a perspective view of a first embodiment of the occluder according to the invention without closure body, in a partially expanded state.

FIGS. 2 to 6 show a first illustrative embodiment of the occluder according to the invention. In FIG. 2, the occluder is shown in a position between a compact state and an expanded state. It also has a virtual longitudinal axis, which is not shown here. A distal axial part 2 and a proximal axial part 3 are arranged along this longitudinal axis. In the examples described here, the two axial parts serve as coupling parts, which can be inserted one inside the other and thus fix the occluder in its expanded position.

The distal coupling part 2 and the proximal coupling part 3 are preferably made of plastic.

The distal coupling part 2 has a distal endpiece 20, which is open on the front. An insert shaft 21 is formed integrally on this endpiece 20 and has a smaller external diameter than the endpiece 20. At its free end, the insert shaft 21 is preferably provided with retaining ribs or lugs. The insert shaft 21 is hollow.

The proximal coupling part 3 is continuously hollow and has an inlet opening and an outlet opening. A proximal endpiece 30 of the coupling part 3 has an external thread. It is adjoined by a receiving sleeve 31, which has a greater external diameter than the insert shaft 21. The insert shaft 21 can be inserted into this receiving sleeve 31 and can be fixed in position by means of the retaining ribs. Several locking positions are preferably possible, in this case three, such that it is possible to choose the distance between the distal endpiece and proximal endpiece.

In the area between endpiece 20 and shaft 21 and between endpiece 30 and sleeve 31, the distal coupling part 2 and proximal coupling part 3 have receiving openings 24 (see FIG. 5) for receiving fixation arms 40.

These fixation arms 40 are part of a deployable or expandable fixation unit 4. The fixation arms 40 are designed as bows and have two branches and, connecting these two branches, a bridge 41. The two branches preferably extend approximately parallel to each other. The bridge is preferably rectilinear. The free ends of the branches are mounted pivotably in the receiving openings 24 of the distal coupling part 2 and proximal coupling part 3. The branch forms the free end of the fixation arm.

Figure 5:
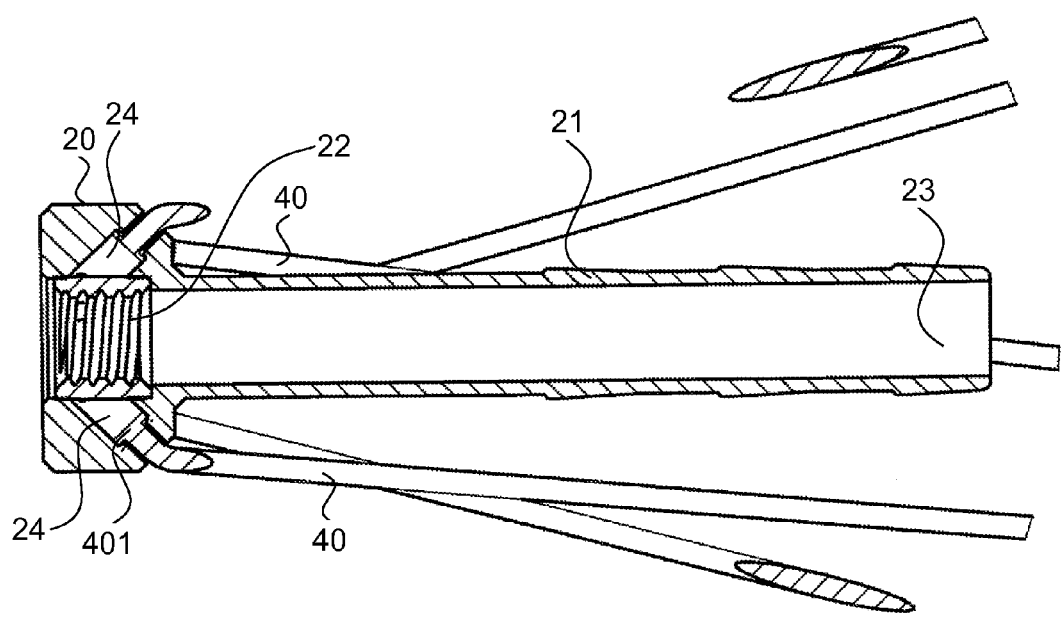
FIG. 5 shows an enlarged cross section through the distal end of the occluder according to FIG. 2, in a side view.

An example of a bearing of this kind can be seen in FIG. 5. Other bearings are possible. The distal coupling part 2 is shown. The proximal coupling part 3 is of the same design as regards the bearing of the arms 40. Receiving openings 24 in the form of stepped holes are present in the coupling part 2, distributed about the circumference thereof. The longitudinal axis of the openings 24 extends at an angle to the longitudinal axis of the occluder and preferably corresponds to the angle of the arms 40 in their expanded position. The branches of the arms 40 are shown curved in this figure. However, they are preferably designed in one piece without curve.

The end is formed by a widening in the shape of a nail head 401. This nail head 401 is engaged in the step of the opening 24, such that the arm 40 is fixed movably in the opening.

As can be seen in FIG. 2, the branches of the arms 40 intersect in their end area, i.e. a branch of a first arm intersects a branch of a second arm in the area where they are secured. In this example, a branch of two adjacent arms 40 is in each case secured between two bows of an arm 40.

Four such fixation arms 40 are preferably present in each case at the distal end and the proximal end of the occluder. However, it is also possible for three or five arms 40 or another number of arms 40 to be present. It is also possible for a different number of arms 40 to be present at both ends.

All the arms 40 are preferably of the same length and of the same width. However, the arms 40 at the proximal end can differ from those at the distal end, for example in size and/or shape. Moreover, the arms at the same end can differ from one another.

The bridge is surrounded by a second sleeve 42, which can turn relative to the bridge about the longitudinal axis thereof. A connecting member 43 is arranged on this second sleeve 42. It is, for example, welded to the latter or adhesively bonded thereto. It is preferably inserted into a bore and held in position with a nail head.

Each bridge is preferably provided with a second sleeve 42, and each second sleeve 42 is provided with a connecting member 43, preferably with exactly one connecting member 43.

Figure 14:
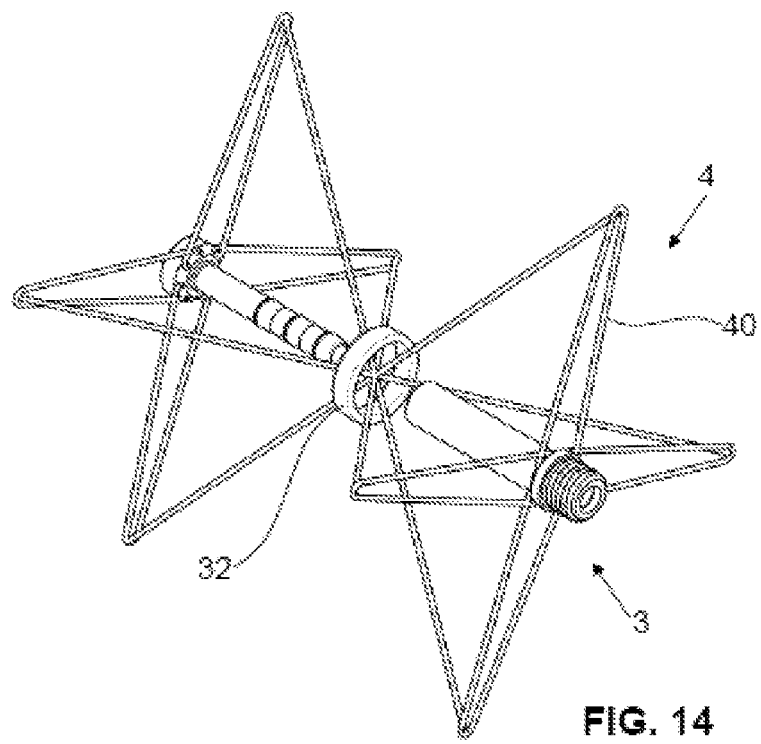
FIG. 14 shows a perspective view of the occluder according to FIG. 9 including a sleeve.

Each connecting member 43 connects a distal fixation arm 40 to a proximal fixation arm 40. This connection is preferably made between two diametrically opposite fixation arms 40, such that the connecting members 43 intersect. However, they also extend independently of one another in the area of intersection. They can be connected loosely to one another in this area via a first sleeve 32, as shown in FIG. 14, which does not however impede their longitudinal displaceability relative to one another inside the first sleeve and relative to the first sleeve 32. Depending on whether the proximal and distal ends of the fixation arms are designed symmetrically or not, the area of intersection is located in the middle between the distal endpiece 20 and proximal endpiece 30 of the occluder or nearer to one or other of these endpieces 20, 30.

The fixation arms 40 are preferably made from wire. Nitinol or a resorbable material is preferred. Preferred diameters of the arms 40 are, for example, 0.1 mm to 0.3 mm, preferably 0.2 mm. The length of the arms 40, measured from the bow 40 to the bridge, is 10 mm to 30 mm for example, preferably 20 mm.

In this example, the second sleeve 42 and the connecting members 43 are also made from a wire, preferably of nitinol or a resorbable material. The connecting wires 43 are preferably of the same thickness and designed like the fixation arms 40. They can have a diameter of 0.1 mm to 0.3 mm for example, preferably of 0.2 mm. Their length is 5 mm to 15 mm for example, preferably 10 mm.

Figure 3:
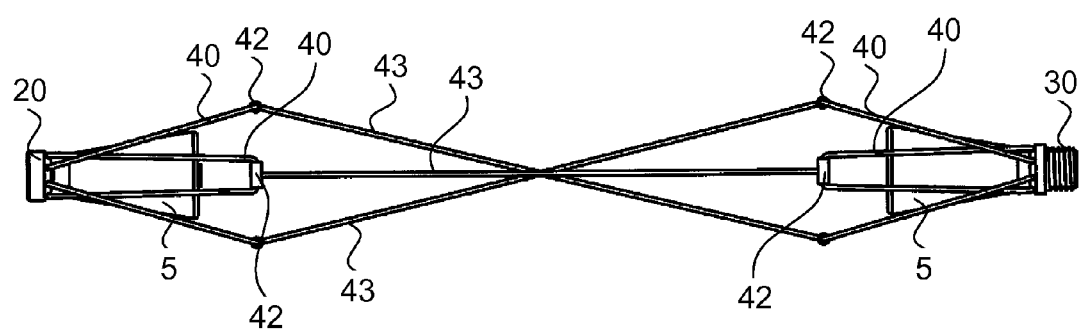
FIG. 3 shows a side view of the occluder according to FIG. 2 with closure body, in an approximately elongate state.

In FIG. 3, this occluder is now shown in the approximately elongate state. In this state, or in a state in which it is even more elongate and therefore more compact in a direction transverse to the longitudinal axis, the occluder is introduced into the human or animal body. To do so, a catheter system is used, as is known in the prior art. An example of how it is introduced is shown in FIG. 6.

Figure 6:
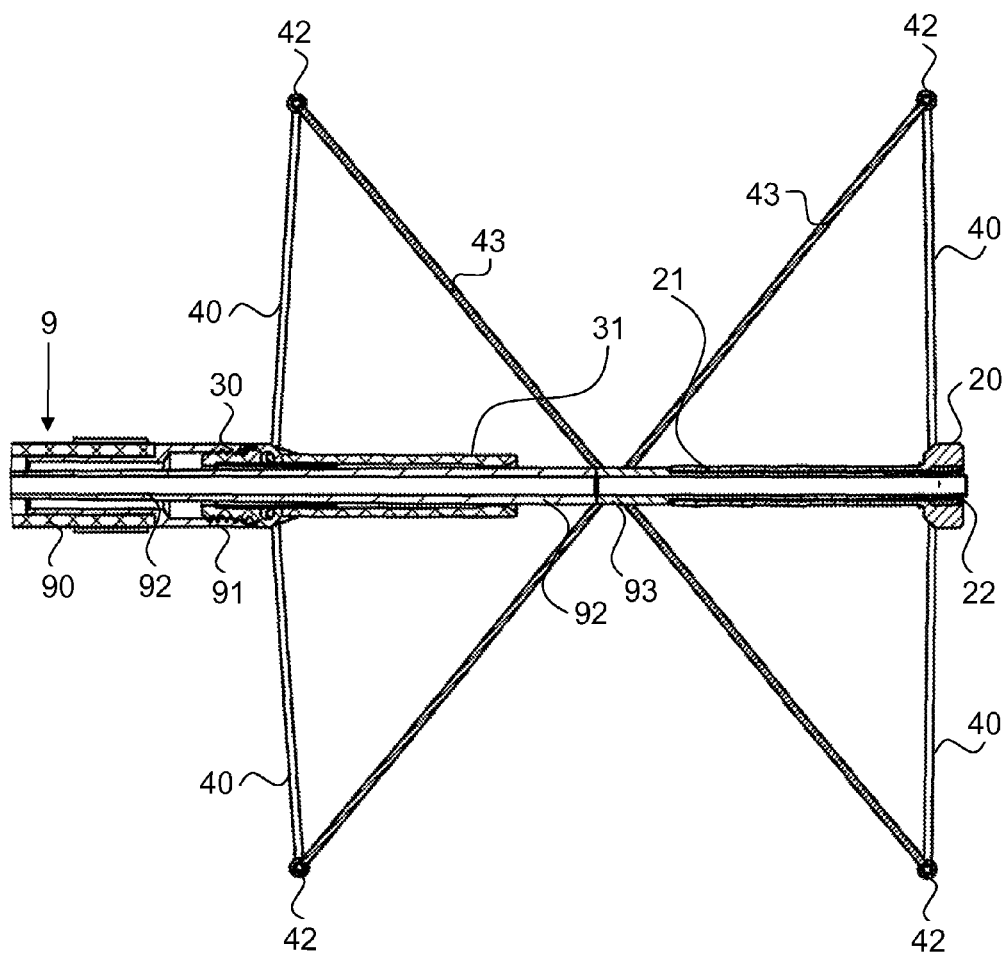
FIG. 6 shows a side view of the occluder according to FIG. 2, with a partially represented catheter system.

In FIG. 6, the catheter system 9 is indicated only by its distal end. The system 9 has a hollow catheter body 90, which is preferably formed by a flexible tube. A stiff head 91 with an internal thread is fitted onto an end of this catheter body 90. With this internal thread, the catheter 9 is connected to the external thread of the proximal coupling part 3 of the occluder.

A flexible catheter tube 92 extends inside the catheter body 90 and passes through the receiving sleeve 31 of the proximal coupling part 3 and merges into a catheter tip 93. This catheter tip 93 reaches into the insert shaft 21 of the distal coupling part 2. The catheter tip 93 is provided with an external thread, which engages in an internal thread 22 of the distal coupling part 2 (see FIG. 5).

The occluder is compressed by means of an axial tensile force, transmitted via the catheter system, being applied to the connecting wires 43. By pulling the distal end of the tube 92 back to the catheter body 90, the occluder is opened out and expanded. Depending on the design, the expansion can take place automatically or by application of force.

An expanded state of this kind can be seen in FIG. 6. The occluder can now be positioned optimally in the passage. Finally, the tube 92 is pulled back even farther, such that the two coupling parts 2, 3 engage one inside the other and fix the occluder in the expanded position. The threaded connections between catheter and occluder are freed and the catheter is removed.

Figure 12:
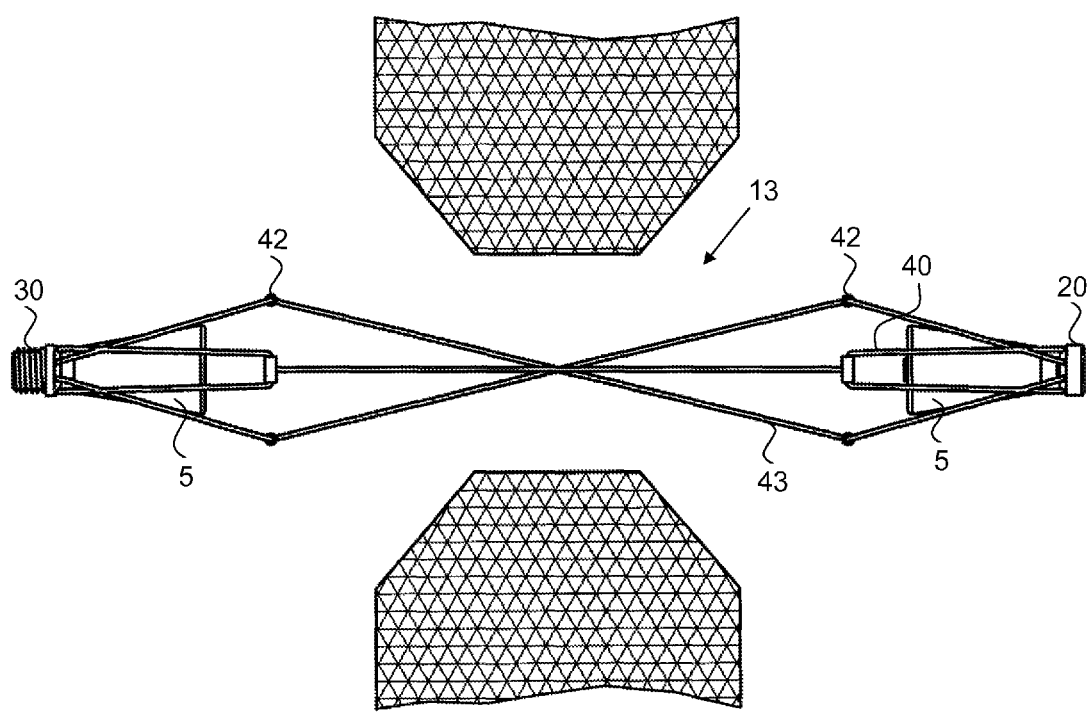
FIG. 12 shows the occluder according to FIG. 3 inserted in a passage.
Figure 13:
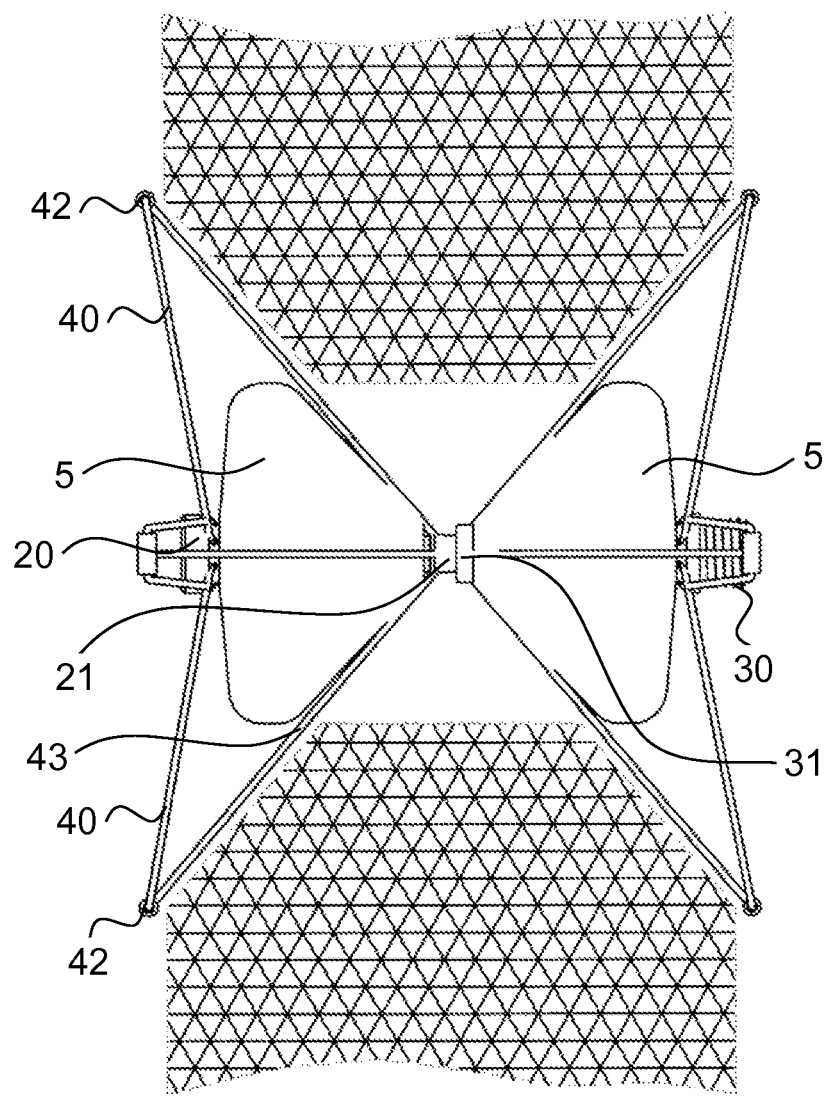
FIG. 13 shows the occluder according to FIG. 12 in the expanded and fixed state.

FIGS. 12 and 13 show the occluder in the defect 13.

Figure 4:
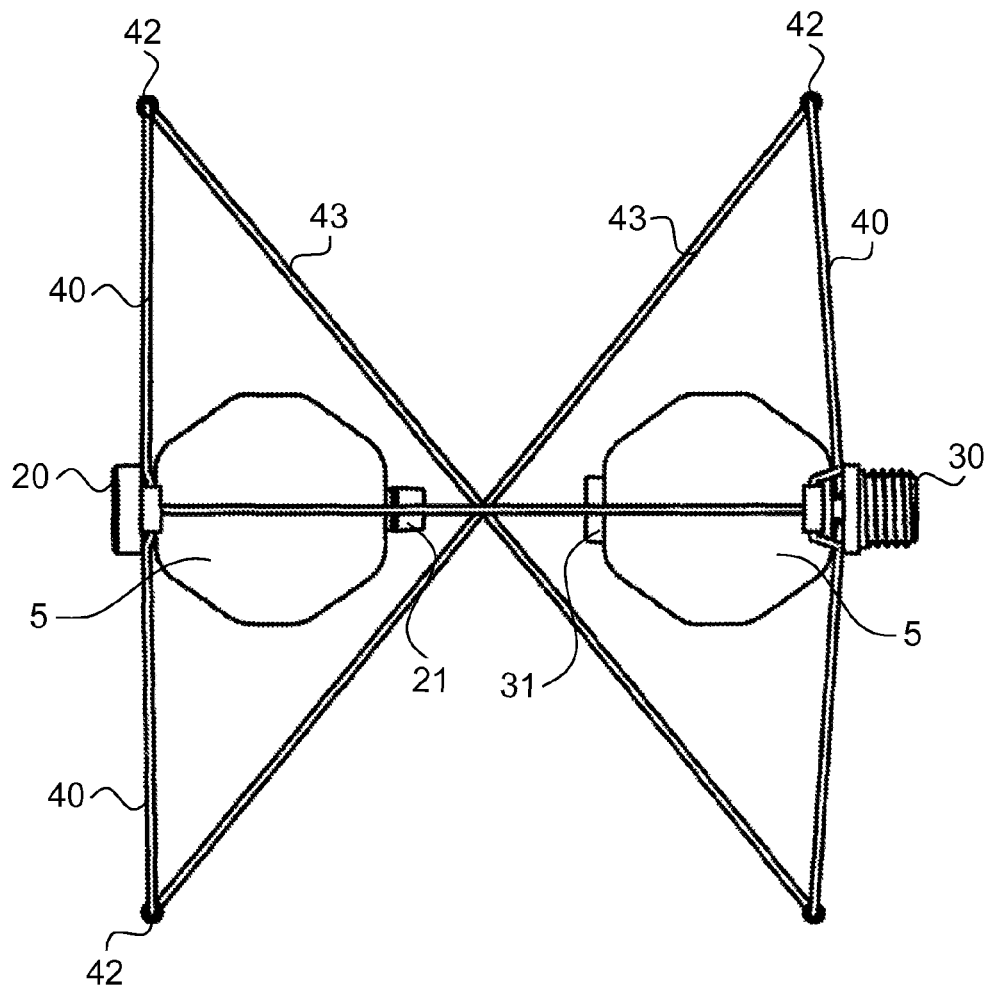
FIG. 4 shows a side view of the occluder according to FIG. 2 with closure body, in a partially expanded state.

FIGS. 3 and 4 show a first example of a closure body 5, as is used with the fixation unit described above. This closure body is a compressible, flexible tampon. In this example, two tampons 5 are present, of which a first tampon 5 is fitted onto the receiving sleeve 3 of the proximal coupling part 3 and a second tampon 5 is fitted onto the insert shaft 21 of the distal coupling part 2. They are preferably welded, sewn or adhesively bonded to these parts 2, 3. However, they can also be fixed in some other way. A suitable tampon 5 is in particular a sponge-like material or a woven material, for example GORE-TEX®. A material is preferably used which is initially permeable to blood, in which case the thrombocytes are caught in the material and the closure body thus becomes impermeable to blood and growth in the defect is initiated.

As can be seen in FIG. 4, the tampons 5 stretch out automatically during the expansion of the fixation unit 4 and they conform to the shape of the defect.

It is also possible for a tampon to be arranged only on one side of the occluder.

Figure 7:
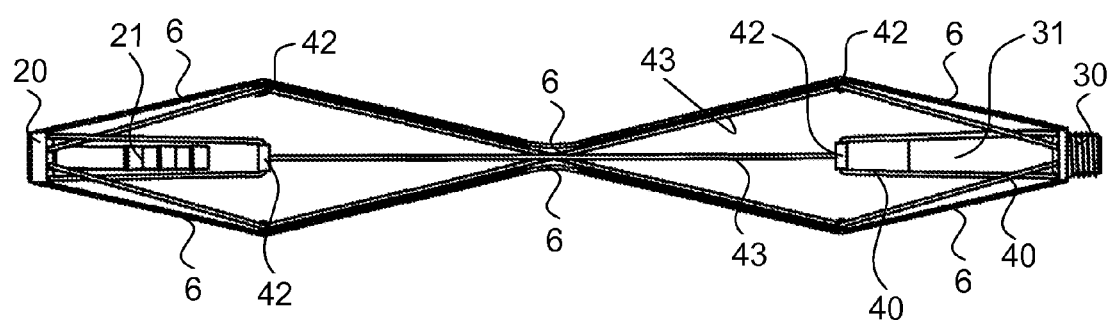
FIG. 7 shows a side view of a second embodiment of the occluder according to the invention in an approximately elongate state, with a balloon sheath.
Figure 8:
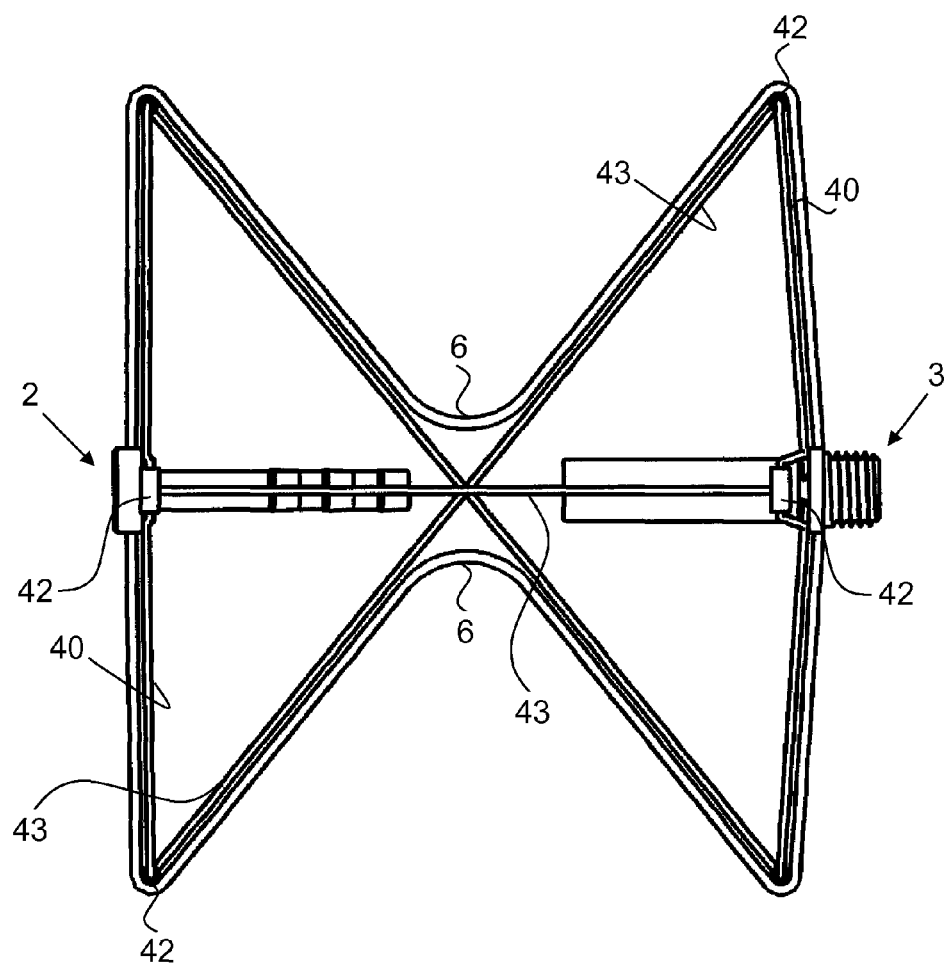
FIG. 8 shows the occluder according to FIG. 7 in a partially expanded state.

FIGS. 7 and 8 show another closure body. The latter is in this case a balloon 6, which is secured to the distal endpiece 20 and proximal endpiece 30 and encloses the fixation unit 4. The balloon 6 is preferably designed as a double balloon with two chambers and with a narrowed connecting area. The balloon 6 is preferably stretched out when the fixation arms 40 are deployed, as can be seen in FIG. 8. The balloon is preferably made of PET, polycarbonate, polyvinyl chloride, PP or silicone. The balloon sheath can also be arranged inside the fixation arms 40 and thus inside the fixation unit 4.

Figure 9:
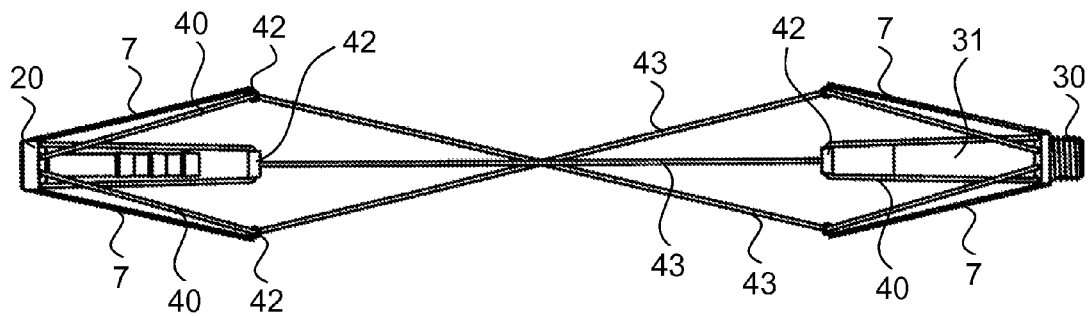
FIG. 9 shows a side view of a third embodiment of the occluder according to the invention in an approximately elongate state, with membranes.
Figure 10:
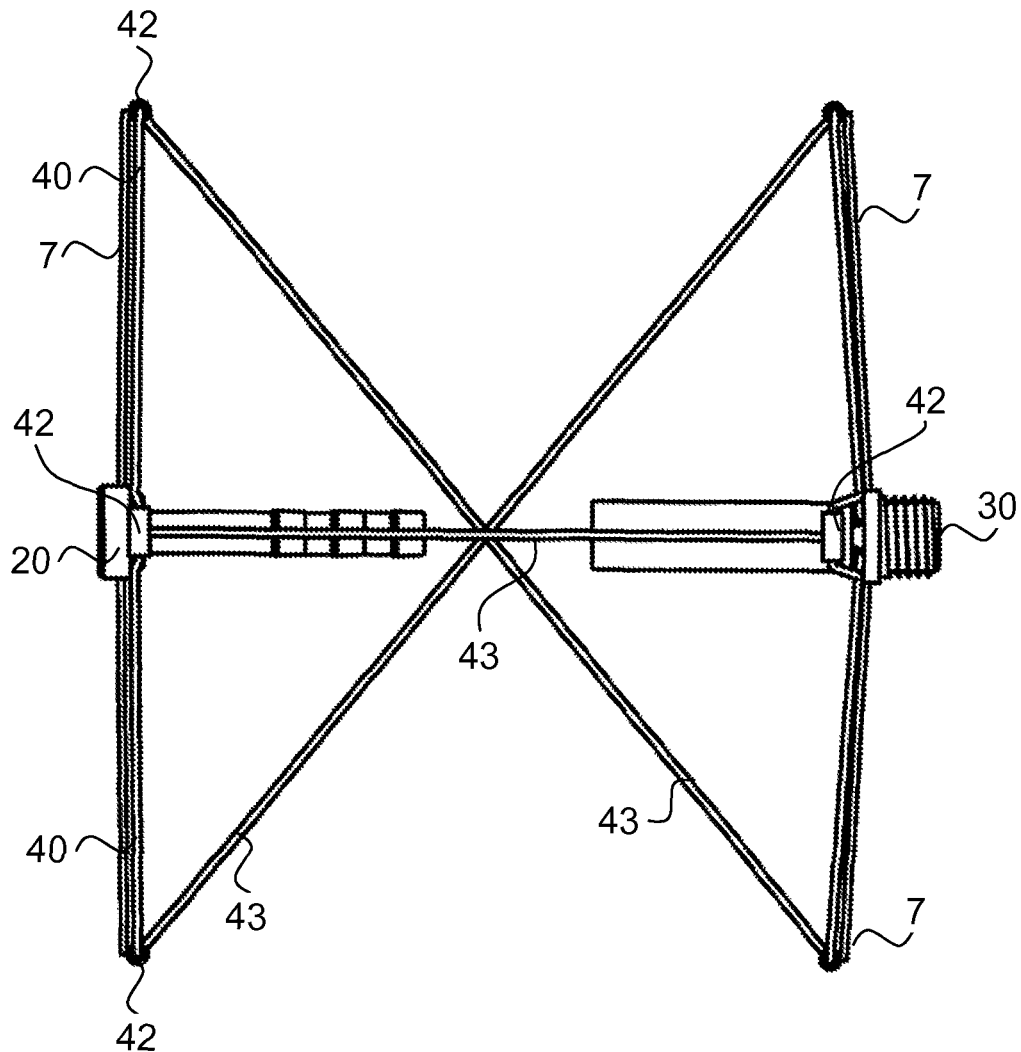
FIG. 10 shows the occluder according to FIG. 9 in a partially expanded state.

FIGS. 9 and 10 show another variant of a closure body. This closure body is a circular membrane 7, for example of PET or DACRON®. The closure body is connected to the fixation arms 40 of the distal or proximal end. In this example, both the distal and also the proximal fixation arms 40 each have a membrane 7. However, it is also possible for a membrane 7 to be present only on one side. The membrane 7 is preferably in each case located on that side of the fixation arms 40 directed toward the corresponding endpiece 20, 30. The membrane 7 can be sewn onto the fixation arms 40, adhesively bonded to them, or connected to them in some other way. As can be seen in FIG. 10, these membranes 7 are stretched out by means of the fixation arms 40. The membranes can also be arranged inside the fixation unit 4, that is to say on the other side of the fixation arms 40.

The various closure bodies mentioned can also be combined with one another in the same occluder.

Figure 11:
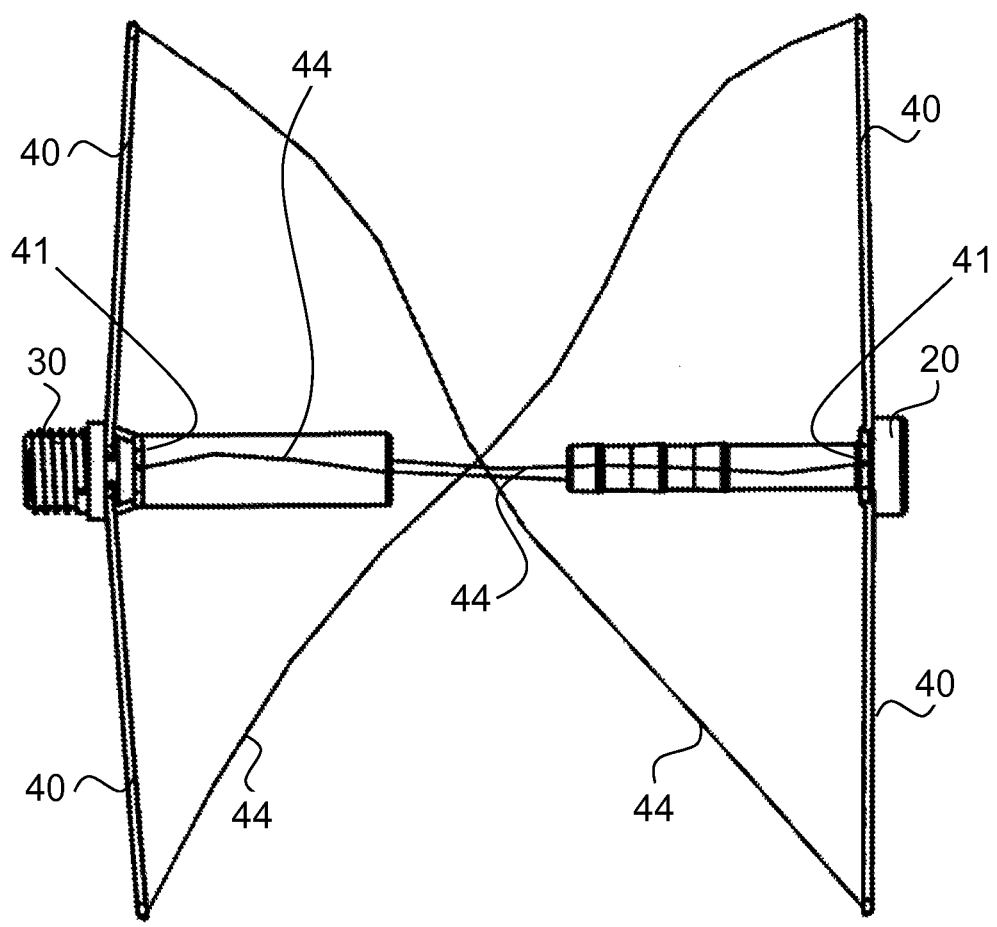
FIG. 11 shows a side view of a fourth embodiment of the occluder according to the invention in a partially expanded state, with connecting strings.

FIG. 11 shows another illustrative embodiment of the occluder according to the invention. It has basically the same structure as the occluders described above, and it can in particular have the above-described closure bodies. However, the occluder has no connecting wires 43, and instead it has connecting strings 44. These can in turn be secured on second sleeves 42, in particular tied on. However, it is preferable for no second sleeves 42 to be present, and the threads or strings 44 are secured directly on the bridges of the fixation arms 40, in particular tied on or adhesively bonded thereto. In this example, in order to ensure that the fixation arms 40 deploy to the expanded position, they are preferably held at an angle, as described above, in the coupling parts 2, 3.

Figure 15:
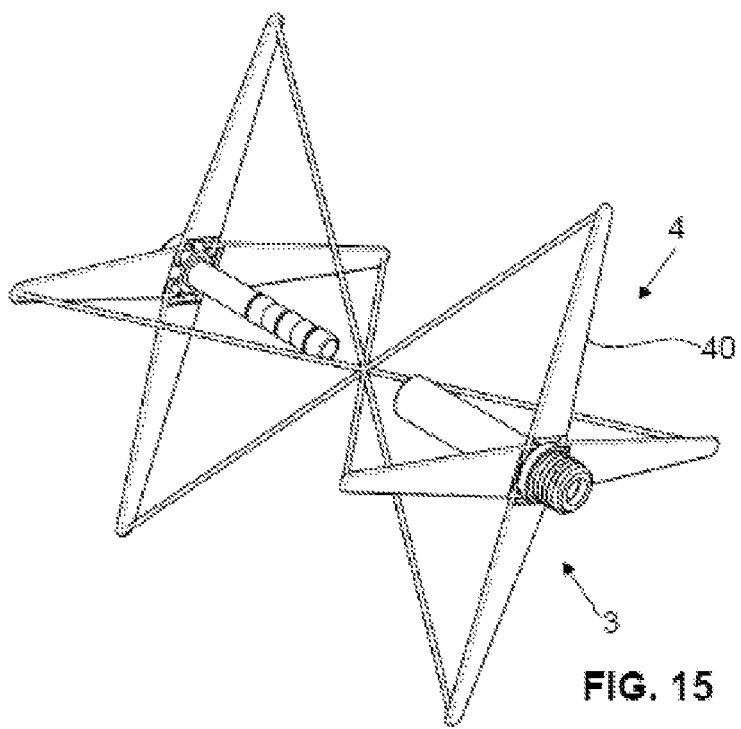
FIG. 15 shows a perspective view of the occluder according to FIG. 9 showing fixation arms as planar elements.

FIG. 15 shows the fixation arms 40 as flat bows or arms.

The invention claimed is:

1. An occluder for closing a passage in a circulatory system, wherein the occluder has an expandable fixation unit for fixing the occluder on the passage, wherein the occluder can be transferred in the passage from a compact form of appearance to an expanded form of appearance, and wherein the occluder has a distal axial part and a proximal axial part, wherein the fixation unit is held pivotably in the distal axial part and the proximal axial part, wherein the fixation unit has distal fixation arms and proximal fixation arms, wherein the distal fixation arms are pivotably connected to the distal axial part and the proximal fixation arms are pivotably connected to the proximal axial part, and wherein the distal and the proximal fixation arms each have a first free end, wherein the first free ends are connected to one another via connecting members that are moveable relative to the fixation arms, wherein each distal fixation arm is connected to one of said proximal fixation arms by one of said connecting members, wherein each of said distal fixation arms and said proximal fixation arms is U-shaped with two branches and a bridge joining the branches wherein the two branches have second free ends which are held pivotably in the proximal or distal axial part, and wherein the bridges form the first free ends of the distal fixation arms and the proximal fixation arms.

2. The occluder as claimed in claim 1, wherein the connecting members extend independently of one another between the individual distal and proximal fixation arms.

3. The occluder as claimed in claim 1, wherein the connecting members intersect in one area, and wherein, in the area, the connecting members extend in an individually displaceable manner in a first sleeve that surrounds the connecting members jointly.

4. The occluder as claimed in claim 1, wherein the bridges are rectilinear.

5. The occluder as claimed in claim 1, wherein each bridge is enclosed by and held pivotably in a second sleeve.

6. The occluder as claimed in claim 5, wherein each connecting member is connected integrally or welded to each respective second sleeve.

7. The occluder as claimed in claim 1, wherein the fixation arms are wires.

8. The occluder as claimed in claim 1, wherein the connecting members are wires or strings.

9. The occluder as claimed in claim 1, further comprising at least one closure body for closing the passage, and wherein the closure body is a membrane, a tampon, or a balloon.

10. The occluder as claimed in claim 9, wherein the closure body comprises a membrane, and wherein the membrane can be brought to the expanded form of appearance by the fixation arms.

11. The occluder as claimed in claim 9, wherein the closure body is a compressible elastic tampon.

12. The occluder as claimed in claim 9, wherein the closure body is a balloon, wherein the balloon extends from the proximal axial part to the distal axial part, and is secured to the two parts and surrounds the fixation arms and connecting members.

13. The occluder as claimed in claim 9, wherein the closure body is arranged in an area that is defined on one side by the distal fixation arms and on an opposite side by the proximal fixation arms.

14. The occluder as claimed in claim 13, wherein the closure body is a tampon.

15. The occluder as claimed in claim 1, wherein the bridges are round.

* * * * *